United States Patent

Owesen

[11] Patent Number: 5,891,399
[45] Date of Patent: Apr. 6, 1999

[54] CLEANING ARRANGEMENT INCLUDING FILTERS AND ULTRAVIOLET RADIATION

[75] Inventor: Yngvar S. Owesen, Hvalstad, Norway

[73] Assignee: Klean As, Norway

[21] Appl. No.: 666,342

[22] PCT Filed: Dec. 1, 1994

[86] PCT No.: PCT/NO94/00194

§ 371 Date: Jan. 17, 1997

§ 102(e) Date: Jan. 17, 1997

[87] PCT Pub. No.: WO95/17634

PCT Pub. Date: Jun. 29, 1995

[30] Foreign Application Priority Data

Dec. 22, 1993 [NO] Norway ................................. 934765
Feb. 25, 1994 [NO] Norway ................................. 934675

[51] Int. Cl.⁶ ........................................... A61L 9/20
[52] U.S. Cl. .......................... 422/121; 96/224; 454/187
[58] Field of Search .......................... 422/24, 117, 107, 422/114, 121; 96/16, 57, 58, 224; 95/69; 454/187

[56] References Cited

U.S. PATENT DOCUMENTS

| | | | |
|---|---|---|---|
| 2,906,104 | 9/1959 | Schaefer et al. | 422/121 X |
| 2,945,554 | 7/1960 | Berly et al. | |
| 3,418,069 | 12/1968 | Decupper | 422/121 |
| 3,576,593 | 4/1971 | Cicirello | 422/121 X |
| 3,674,421 | 7/1972 | Decupper | 422/121 |
| 4,049,400 | 9/1977 | Bennett et al. | 422/4 X |
| 4,118,191 | 10/1978 | Böhnensieker . | |
| 4,210,429 | 7/1980 | Golstein . | |
| 4,400,270 | 8/1983 | Hillman | 422/24 X |
| 4,673,848 | 6/1987 | Hagiwara et al. | |
| 4,766,321 | 8/1988 | Lew et al. | |
| 4,909,040 | 3/1990 | Feltrin . | |
| 4,990,313 | 2/1991 | Pacosz . | |
| 5,019,804 | 5/1991 | Fraden . | |
| 5,114,670 | 5/1992 | Duffey . | |
| 5,185,015 | 2/1993 | Searle . | |
| 5,225,167 | 7/1993 | Wetzel . | |
| 5,330,722 | 7/1994 | Pick et al. | 422/121 X |
| 5,369,892 | 12/1994 | Dhaemers | 34/275 |

FOREIGN PATENT DOCUMENTS

| | | |
|---|---|---|
| 461 310 A1 | 12/1991 | European Pat. Off. . |
| 25 39 743 | 3/1977 | Germany . |
| 27 33 729 | 9/1979 | Germany . |
| 28 17 772 | 10/1979 | Germany . |
| 28 44 997 | 4/1980 | Germany . |
| 3637702 A1 | 5/1988 | Germany . |
| 533810 | 2/1973 | Switzerland . |
| 1 400 519 | 7/1975 | United Kingdom . |
| 1 421 495 | 1/1976 | United Kingdom . |
| 1 540 752 | 2/1979 | United Kingdom . |

OTHER PUBLICATIONS

Dickenson, T. Christopher. Filters and Filtration Handbook, 4th ed, p. 630, 1997.

*Primary Examiner*—Elizabeth McKane
*Attorney, Agent, or Firm*—Burns, Doane, Swecker & Mathis LLP

[57] ABSTRACT

A device used in an air purifying system. The device includes an ultraviolet radiation source, a pre-filter, and a post-filter. The pre-filter is arranged adjacent to the ultraviolet light source such that the pre-filter is irradiated by the ultraviolet light source to destroy bacteria, virus, or other organisms on the pre-filter. The device also includes a cover that is movable between an open and closed position. In the closed position, the device operates in a passive mode to irradiate air within the device and to filter air through filters in the device. In the open position, the device operates in an active mode to irradiate an area external of the device and to simultaneously filter air through a filter in the device.

13 Claims, 11 Drawing Sheets

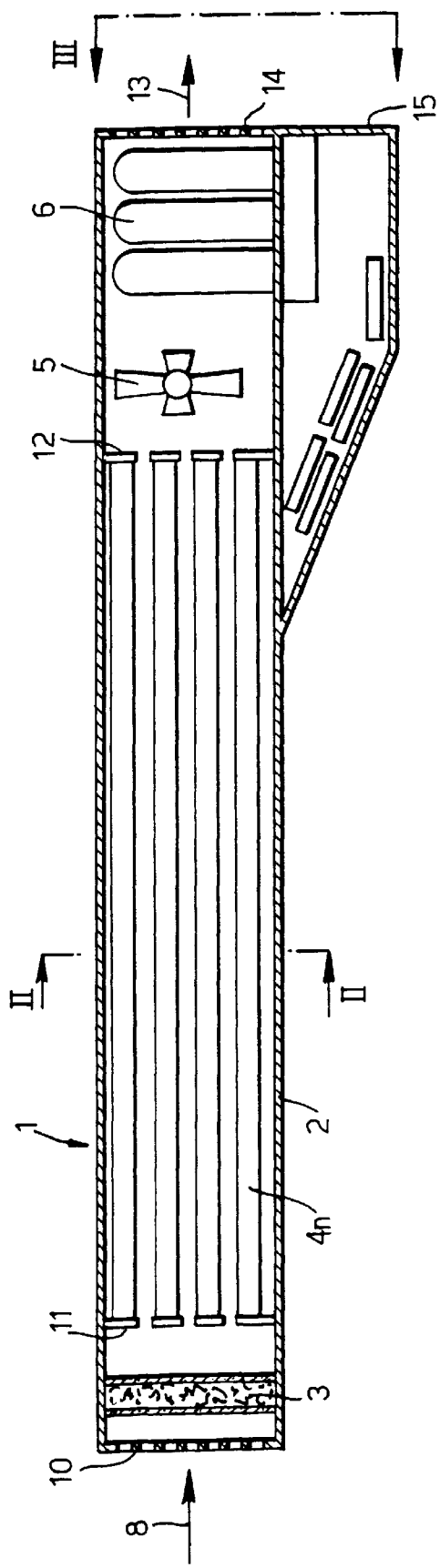
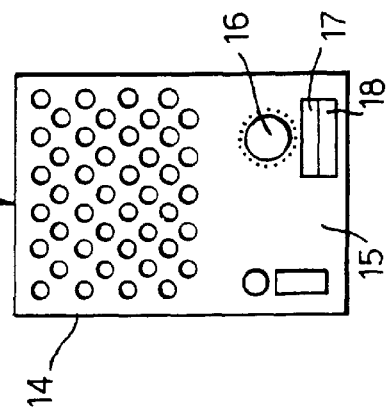
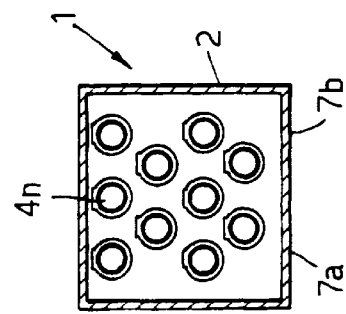

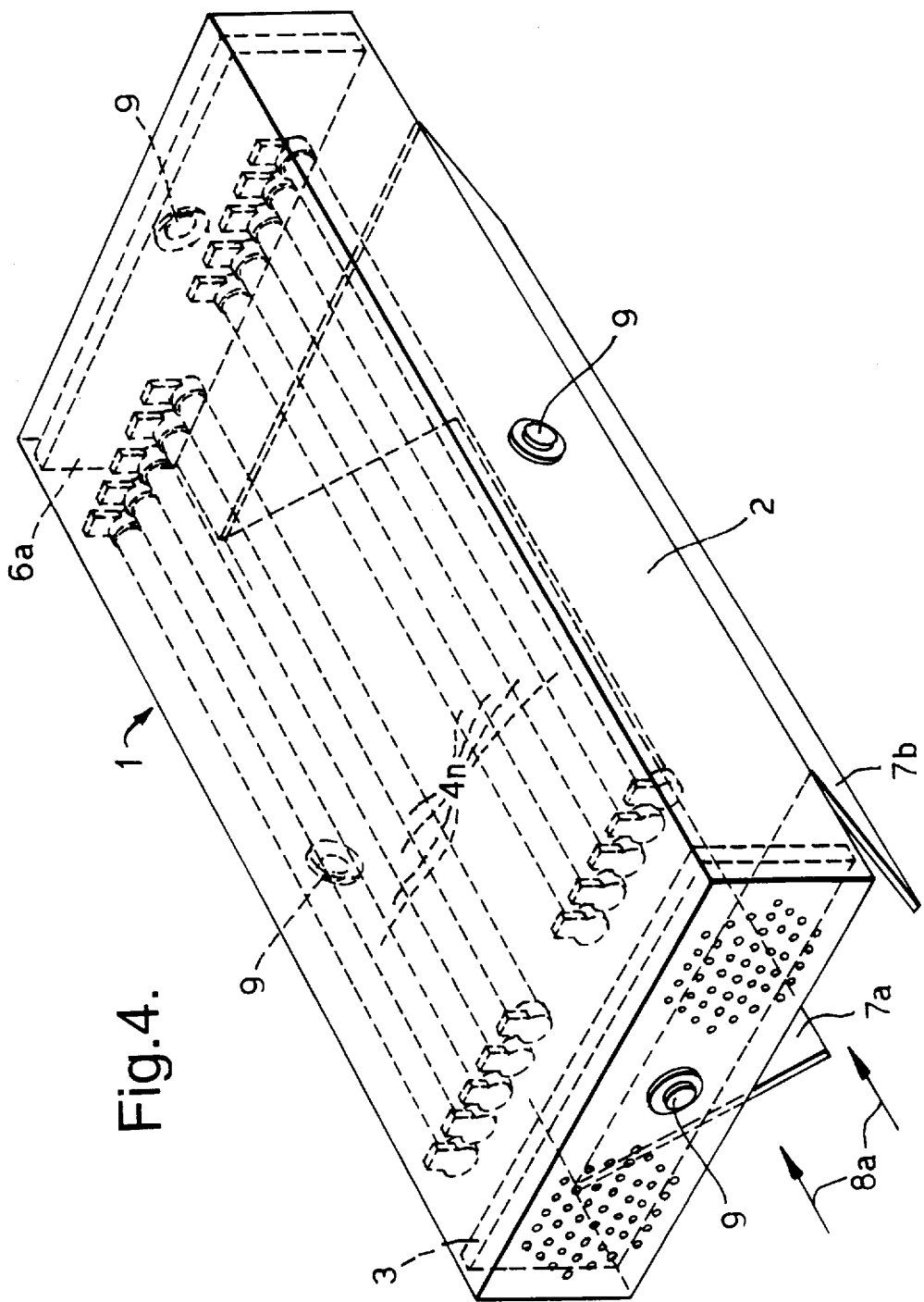

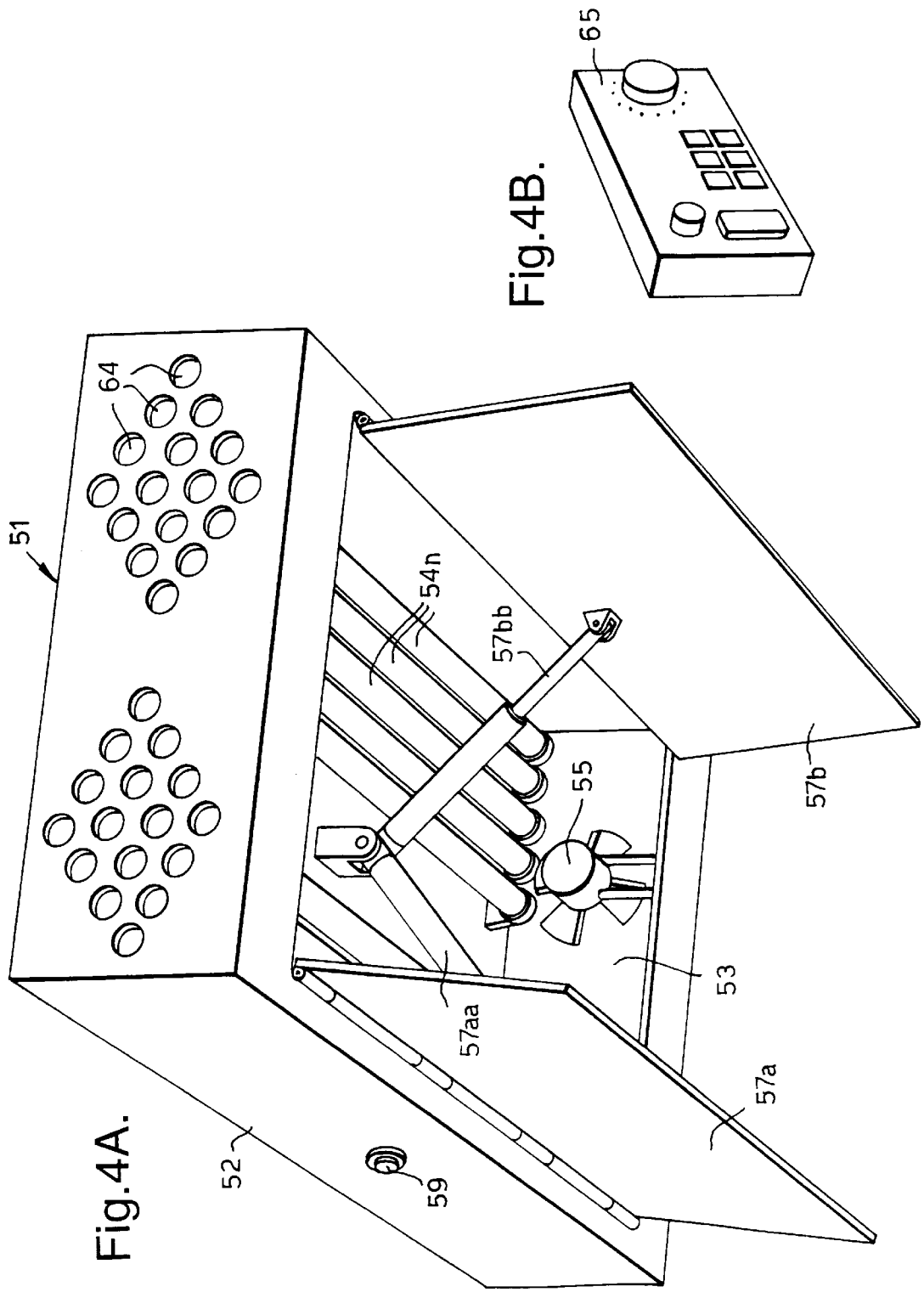

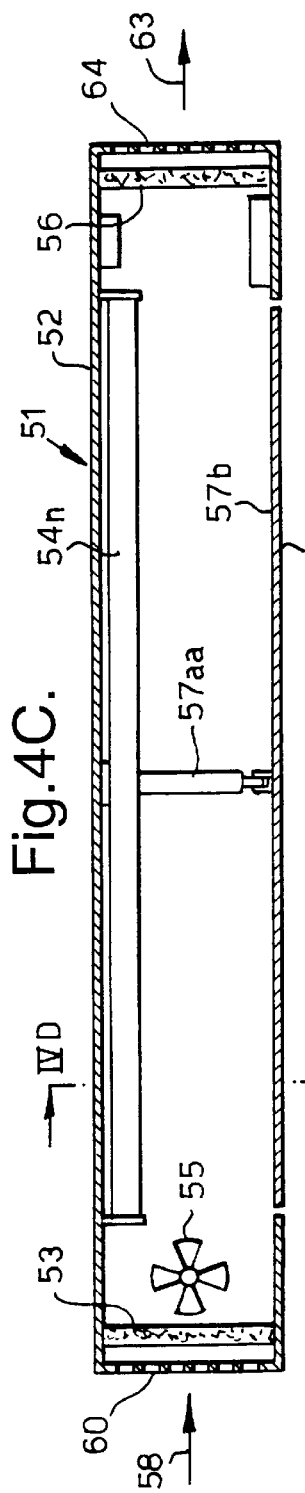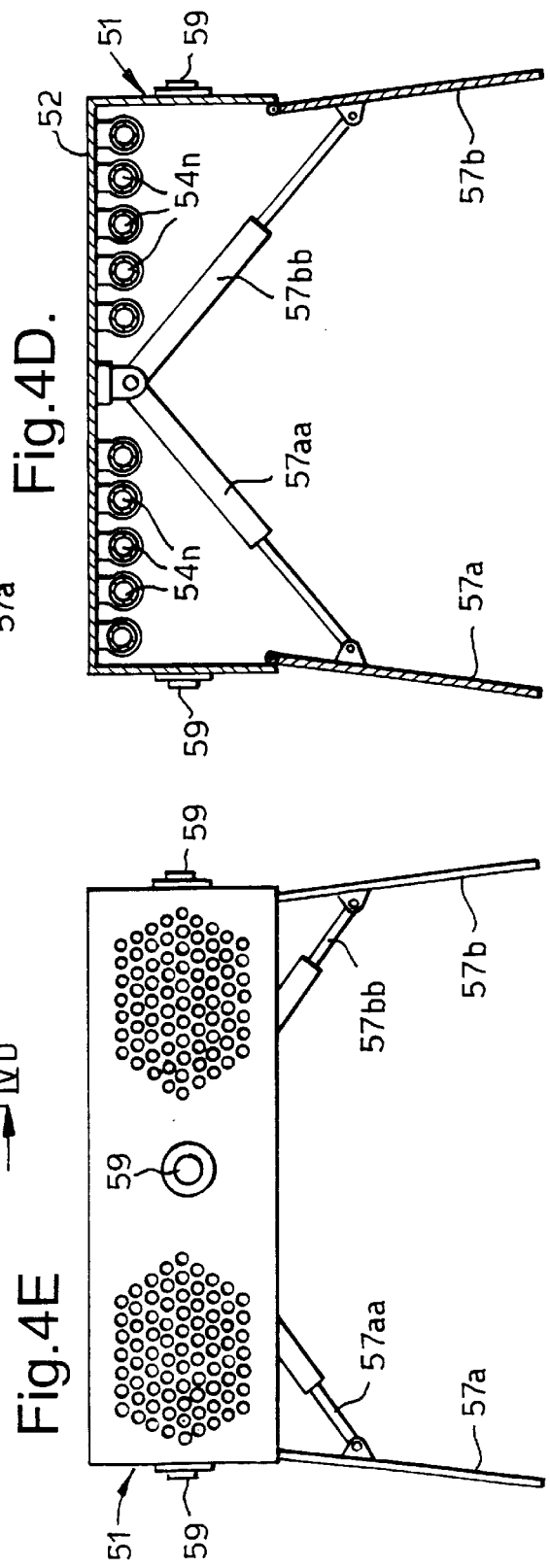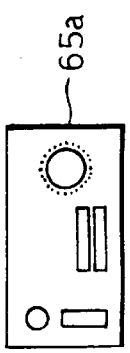

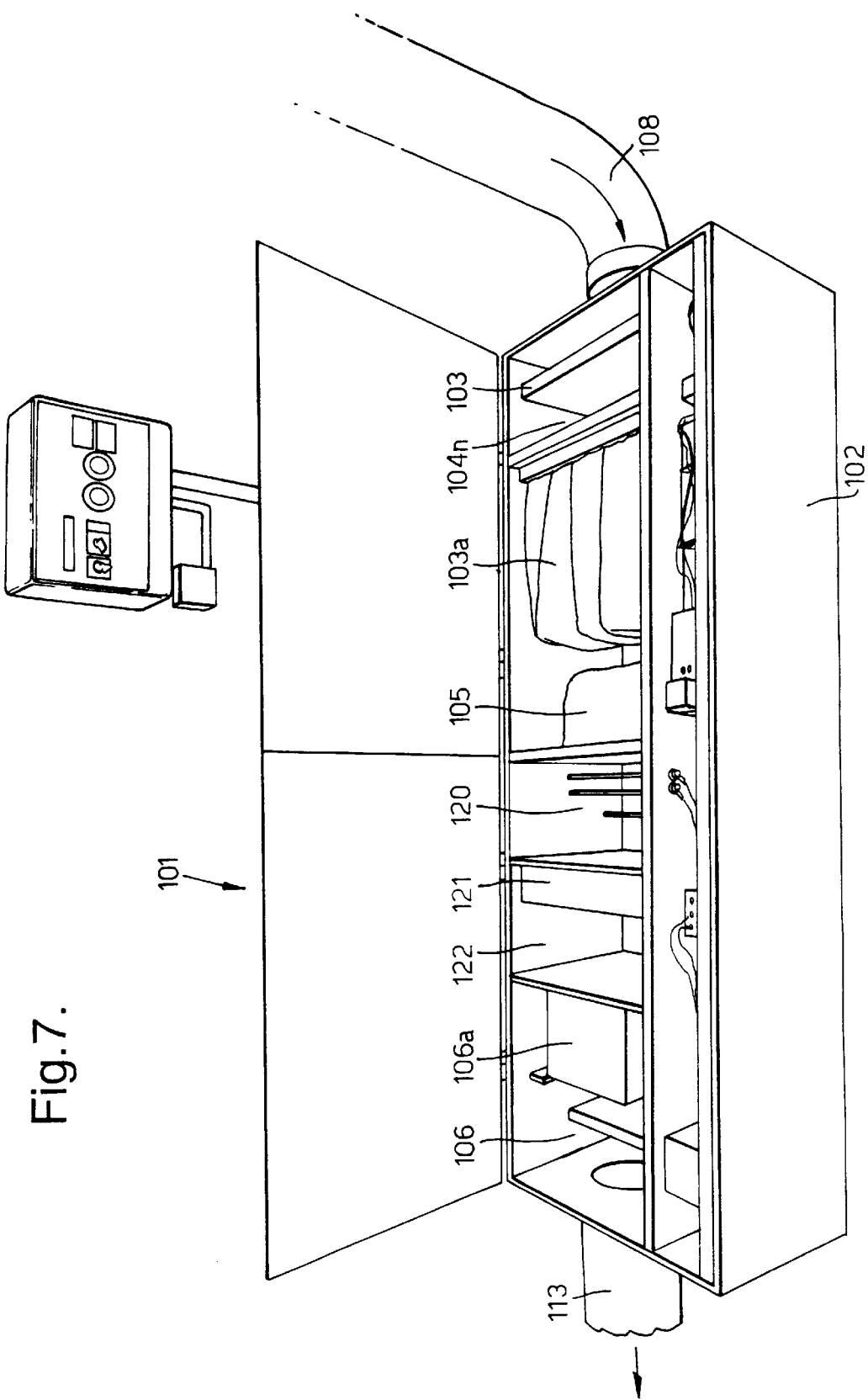

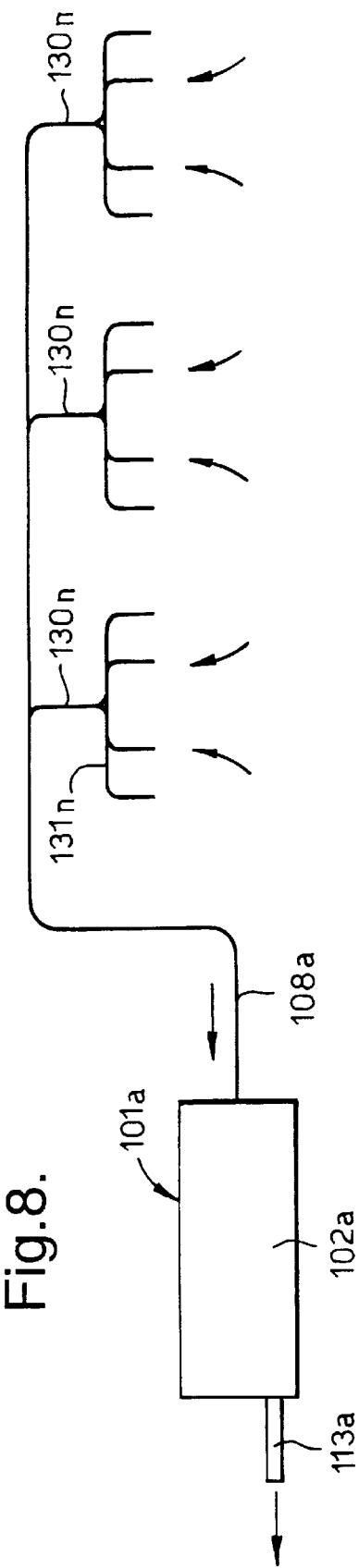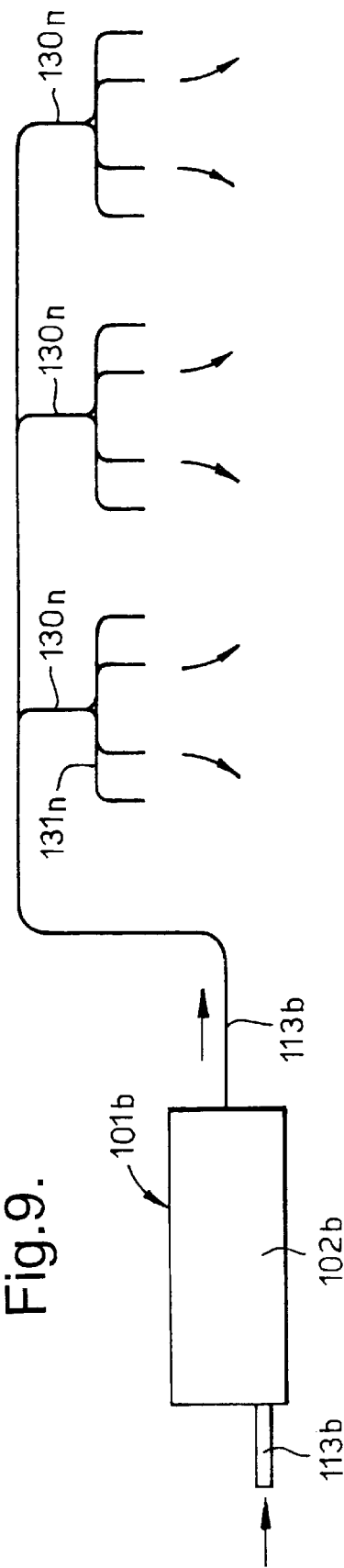

CLEANING ARRANGEMENT INCLUDING FILTERS AND ULTRAVIOLET RADIATION

FIELD OF THE INVENTION

The present invention relates to an arrangement in a purifying system, especially purification related to micro particles and micro organisms, comprising a base means carrying filter means and UV sources.

BACKGROUND OF THE INVENTION

The requirement for purifying air as regards micro particles and micro organisms is continuously increasing, both in private homes, official buildings, restaurants, hospitals, nutrient manufactures, etc.

PRIOR ART

It is previously known that ultra violet rays within certain wavelength can destroy all forms of micro organisms as well as making irreversible damage to superior creatures if the intensity and the duration of the radiation is above a certain level.

For example, in operating rooms there is used UV radiation for sterilizing instruments and furniture, but in such cases said UV sources are too few or positioned in such a way that the radiation does not cover the surfaces or objects in question. There are also previously known water purification systems including UV radiation.

Further, there are known various types of mechanical filters, for example so-called absolute filters having a selectivity degree above 99,9%, but such filters will without frequent exchange and separate sterilization constitute a hotbed of further development of fungi, bacteria or virus.

It is also previously known to use corona discharge for purifying air, so-called bioclimatics, wherein the air passes a corona discharge for combined purification and sterilisation of the air, as well as a refreshment of the oxygen molecules.

DISCUSSION OF THE INVENTION

An object of the present invention is to provide a arrangement in a purifying system in which the combination of previously known cleaning methods can provide a substantially better result, at the same time as the arrangement in a simple manner can be adapted to various fields of application.

This is achieved in an arrangement of the type as stated in the preamble, which according to the invention is characterized in that said base means are equipped with preferably remotely controlled means which upon appropriate signal can bring the base means to, on the one side, take a completely or partly passive mode for harmless UV covered purification/radiation of air, and, on the other side, take an active mode for especially UV exposed radiation of objects and room surfaces, and preferably in combination with purification of room air.

Especially in connection with the utilization wherein the purification system also is to effect direct UV radiation of the room in question and the objects being housed therein, the invention is characterized in that said base means are constituted by housing means comprising one or more controlled covers which through appropriate signal take a closed position for UV covered purification/radiation of air and an open position for combined UV exposed radiation of objects and room surfaces and purification of air, respectively.

It may be appropriate that said housing means is arranged for ceiling mounting, wall mounting, stand-alone mounting, or a combination thereof, for by the combination of several housing means to render full UV radiation of all surfaces/objects in a room.

Alternatively, an embodiment may be to the fact that said preferably remotely controlled means are provided for displacing said arrangement in the room in question.

In connection with other embodiments one housing means can be provided as a central first aggregate, said aggregate comprising an inlet pipe sucking impure air to the housing means via a plurality of branches included in a ventilation system, for example branches which are designed as ornament objects and/or utility objects in a living room, for example a restaurant.

A variant of such an aggregate can be to the fact that said aggregate comprises an outlet opening which by over pressure blows out from said aggregate cleaned air from said housing means via a plurality of branches included in a ventilation system, for example via branches designed as ornament objects and/or utility objects in a living room, for example a restaurant.

By combining such a blowing aggregate and such a sucking aggregate the output air form the second aggregate can be connected to the inlet to the blowing aggregate, possibly in combination with a heat exchanger and a fresh air intake.

Further features and advantages in the present invention will appear form the following description taken in connection with the appended drawings, as well as from the appended patent claims.

BRIEF DISCLOSURE OF THE DRAWINGS

FIG. 1 is a side view partly in section of a first embodiment of an arrangement according to the invention.

FIG. 2 is a section taken along the line II—II in FIG. 1.

FIG. 3 is an end view seen in the direction of the arrows III—III in FIG. 1.

FIG. 4 is a perspective, schematic view of the main elements which are included in an embodiment similar to that which is illustrated in FIG. 1.

FIG. 4A illustrates perspectively as seen from the "underside" an embodiment similar to the embodiment illustrated in FIG. 4, comprising controllable covers in open position.

FIG. 4B illustrates perspectively a possible separate control panel for the embodiment according to FIG. 4A.

FIG. 4C is a side view partly in section through the embodiment illustrated in FIG. 4A.

FIG. 4D is a section taken along the line IVD—IVD of FIG. 4C, comprising controllable covers in open position.

FIG. 4E is a front and view of the embodiment according to FIG. 4C.

FIG. 4F illustrates an alternative or possibly built-in control panel of the embodiment according to FIG. 4c.

FIG. 7 is a perspective illustration of a further embodiment of the arrangement according to the invention.

FIG. 8 illustrates a first application of the embodiment illustrated in FIG. 7.

FIG. 9 illustrates a second application for the embodiment illustrated in FIG. 7.

DESCRIPTION OF EMBODIMENTS

Figure 5:
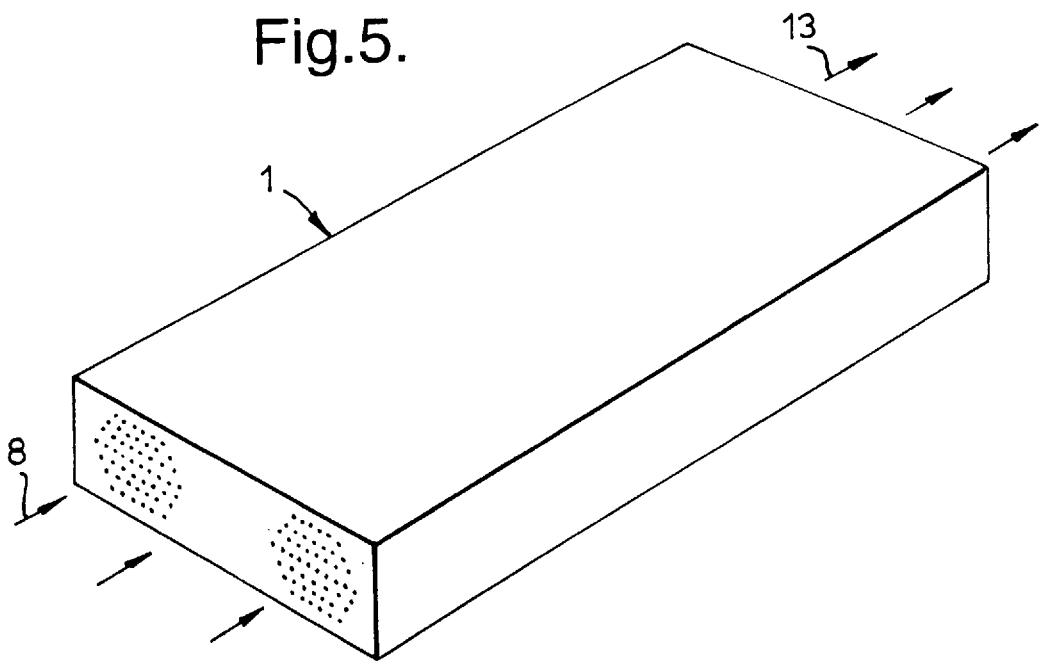
FIG. 5 is a simplified view illustrating an embodiment of the arrangement according to the invention in closed position.

In the embodiment of an arrangement in a purifying system according to the invention, which is illustrated in FIGS. 1–4, the arrangement itself is designated by reference numeral 1, and this arrangement comprises a housing means 2 housing a pre-filter 3, one or more UV radiation sources 4n, one or more fans 5 as well as a post-filter 6, all of which has been combined for purification and radiation of room air in the room, chamber or hall wherein the arrangement is mounted.

Figure 6:
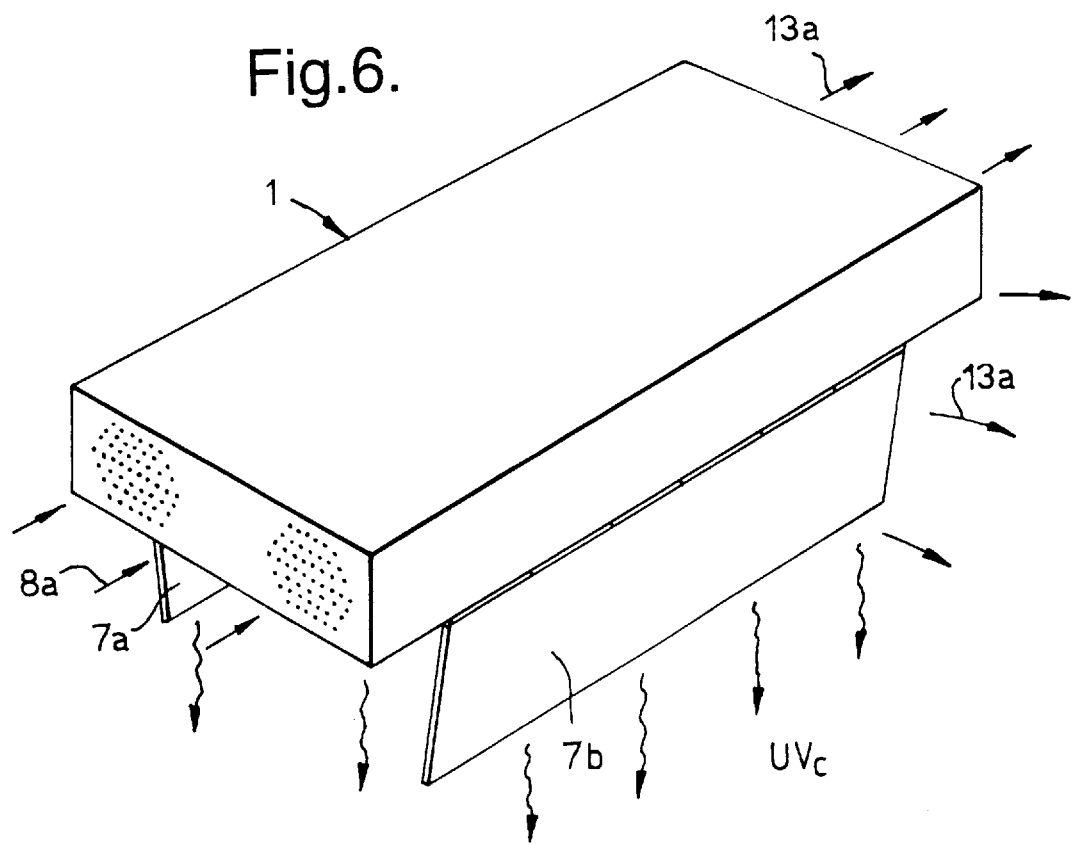
FIG. 6 is a schematical perspective view similar to FIG. 5, but illustrates the arrangement in open position.
Figure 6A:
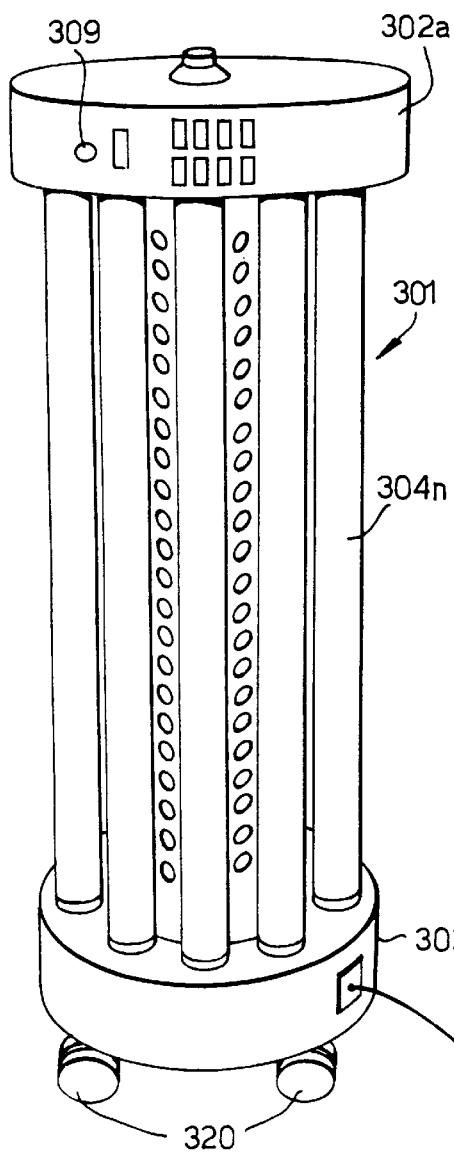
FIG. 6A illustrates perspectively a free-standing mobile embodiment of the invention.
Figure 6D:
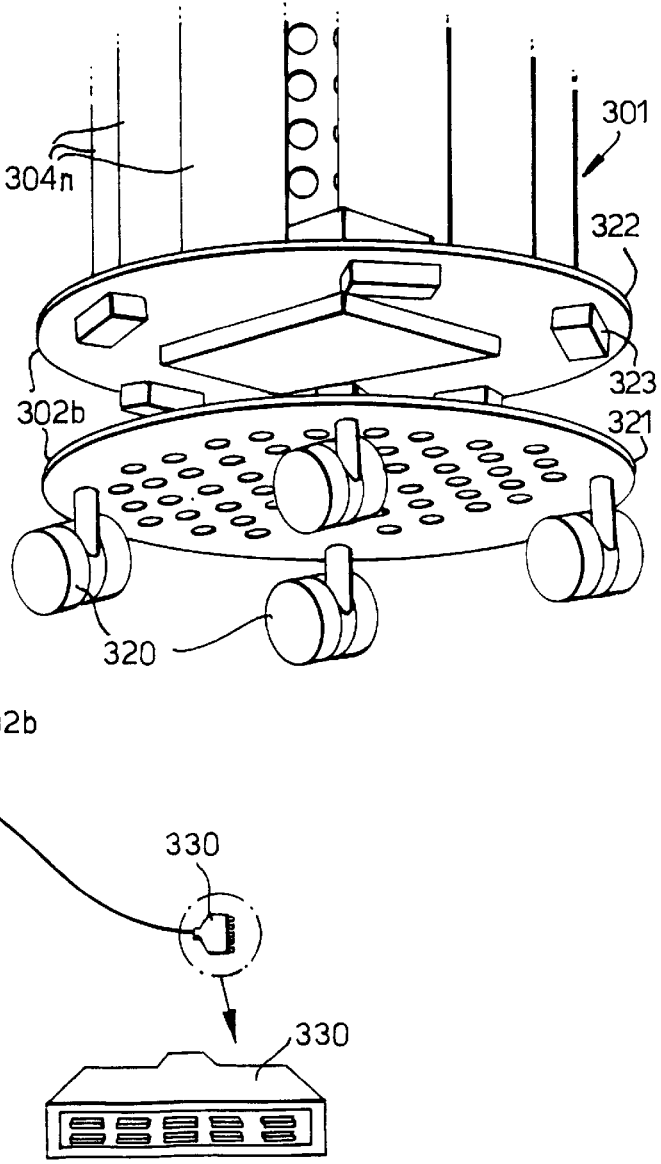
FIG. 6D illustrates perspectively on a larger scale details of the lower part of the embodiment according to FIGS. 6A, 6B.
Figure 6B:
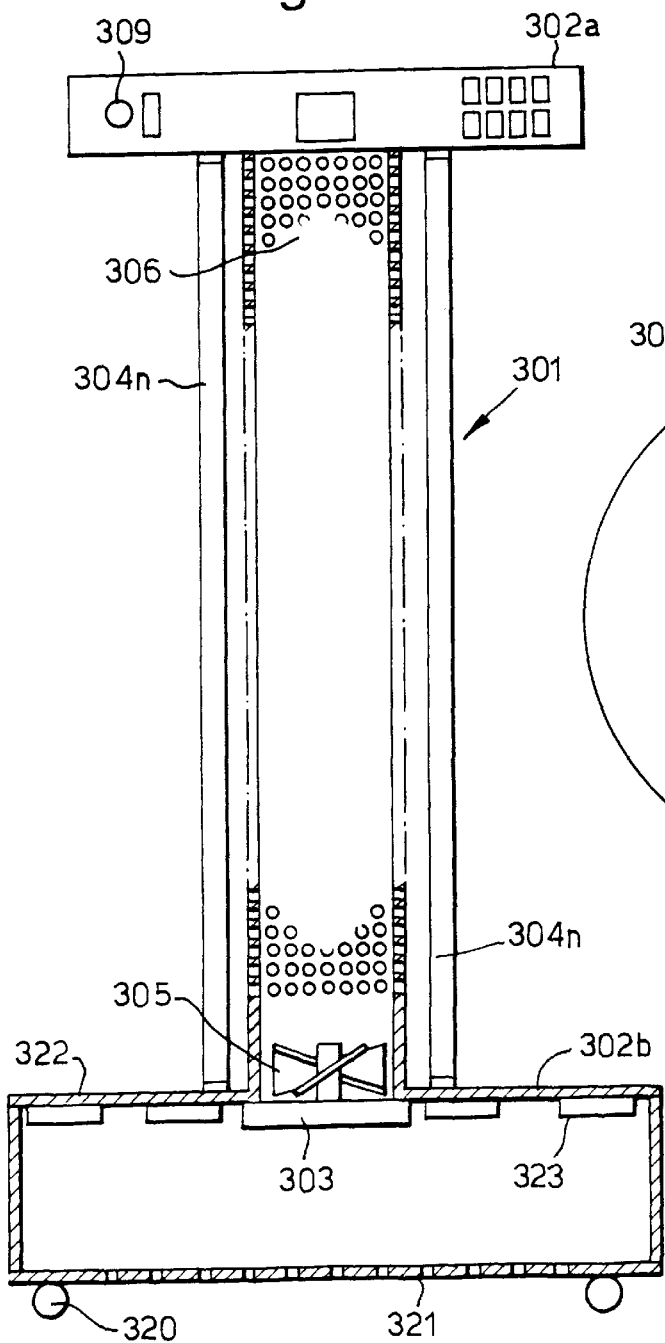
FIG. 6B illustrates a front view partly in longitudinal section of the embodiment according to FIG. 6A.
Figure 6C:
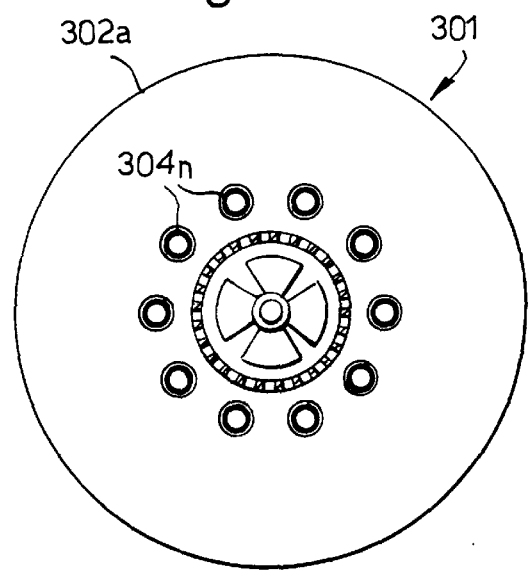
FIG. 6C is a view as seen from above of the embodiment according to FIGS. 6A, 6B.

Especially in connection with the arrangement according to FIG. 1–4, and as more clearly illustrated in FIG. 4, the housing means 2 comprises covers 7a, 7b which by appropriate signal take a closed position for closed purification/radiation of the air 8 being drawn through the housing by means of the fan 5, see especially FIGS. 1 and 5, and an open position, see especially FIGS. 4 and 6, for combined UV exposed radiation of room surfaces and objects in the room in question, as well as purification of the room air 8a passing through respectively by the arrangement 1 itself by this position of the covers 7a, 7b.

It is to be understood that the controlled covers 7a, 7b can be connected to driving means of pneumatic, hydraulic, electric or magnetic art, or similar, possibly in combination, and these driving means will come into action for opening said covers 7a, 7b when the room has been detected empty for human beings and animals, such driving means or special closing means being effective for closing purpose upon detection or observation of human beings or animals.

Appropriately, said arrangement can comprise detecting means of IR-type, or similar, for example located at the sides of the housing, as this is illustrated in FIG. 4 by reference numeral 9. Possibly, such IR-detectors 9 can be connected for preventing the opening of said covers 7a, 7b upon observation of human beings and animals.

More specifically the arrangement illustrated in FIG. 1 may comprise a pre-filter 3, for example an EU4-filter preventing direct or reflected UV radiation through the inlet side.

Further specifically the arrangement 1 comprises at the inlet end a perforated grate 10 which incoming air 8 must pass before said pre-filter 3, as well as a perforated plate 11 constituting the one mounting wall for the UV sources 4n, which UV sources extend as longitudinal, parallel UV tubes, which at their second end is mounted in a second perforated plate 12. Thereafter, in the air flow direction, said fan 5 follows, as well as the post-filter 6 which preferably can be a bioclimatic filter, i.e. a corona discharge means which the outgoing air 13 passes for removal of odour, oxygen renewal as well as possible collection of dust, virus, fungus spores and anything else.

The outlet air 13 passes through a filter grid 14 which at the bottom is prolonged to a control plate 15 comprising control lamps, off/on button, means 16 for bioclimatic regulation, as well as hour counter 17 for said UV sources 4n, as well as hour counter 18 for said corona sources 6 for bioclimatic discharge.

As appearing from FIGS. 1 and 5 said housing means 2 is here sealed and free from direct or indirect radiation from said UV sources, i.e. when it is in operation with said covers 7a, 7b closed, which involves that also human beings and animals can reside in the same room as the arrangement without being unfavourably influenced by the UV sources.

In the housing means 2 there can be provided from one to three fans which are protected by a filter medium which otherwise prevents the radiation of UVc rays.

Fine particles which adhere to the filter will be constantly radiated, such that bacteria and virus on said particles will be destroyed.

Lesser particles, from 0.5–0.01 µm, carrying virus and bacteria, will be exposed to a severe UVc radiation in the air flow passing through said housing means 2, said radiation being dimensioned for air velocity up to 4 m/s with 100% sterilisation effect.

The housing means can be designed for operation mounted at the ceiling or on a wall, or in any other manner, and can then be operative when people are working in the room because the covers will then be in a closed position.

When the room is empty without human beings and animals, said covers 7a, 7b are allowed to be opened and a direct radiation on working surfaces and walls and floor can then be effected, as well as other objects possibly being in the room, said fans providing circulation of the air 8a, 13a in the room, see specifically FIGS. 4 and 6.

It is to be understood that the pre-filter 3 resides in a chamber which can also give room for all types of filter, including electrostatic filters, which electrostatic filters can possibly be positioned downstreams of the bioclimatic filter.

At the outlet portion of said housing means 2, i.e. in the area of the perforated grate 14, there may possibly be provided a carbon filter 6a having its own perforated cover plate, see FIG. 4. This carbon filter 6 can be used alone or in combination with the bioclimatic filter.

It is also to be understood that the covers 7a, 7b can appropriately be provided with rubber gaskets.

Further, it is to be understood that the number of covers can be varied from one to several, and also the shape of the covers can be varied within wide limits.

In order to achieve radiation in the room wherein said housing means of various types are mounted, such housing means could according to the invention be provided for ceiling mounting, wall mounting, as free-standing units, or a combination thereof, for by such combination of such housing means to give complete UV radiation of all surfaces in a room, but then when it is observed or registered that no human being or animal are present in the room.

By the embodiment as illustrated in FIGS. 4A–4F, the arrangement itself is designated by reference numeral 51, comprising a housing means 52 including end grates 60, 64 holding a pre-filter 53, for example an EU3 filter a plurality of UV radiation sources 54n, one or more fans 55, as well as a post-filter 56, and also controllable covers 57a, 57b which upon appropriate signal take respectively a closed position, see FIG. 4C, for closed purification/radiation of the air 58 which is drawn through said housing means 52 by means of said fans 55, and an open position, see specifically FIGS. 4A, 4D, 4E for combined UV exposed radiation of room surfaces and objects in the room in question, and simultaneously purification of the room air 63 passing through or by the arrangement 51 itself by open position of said covers 57a, 57b which can be driven by telescope-like arms 57aa, 57bb, for example by means of a vacuum pump (not shown).

Also by this embodiment it has been used for example IR detectors 57 located on the side of the housing means 52, which detectors communicate with control means 65, see FIG. 4b, which for example can be arranged separate in relation to the arrangement 51 itself, or communicate with a second type of control panel 65a which possibly can be built into said arrangement 51 in a suitable manner.

It is to be understood that the type of pre-filter and post-filter can be varied within wide limits, and it is also to be understood that the arrangement 51 can comprise electrostatic filters, bioclimatic filters, etc., depending on the conditions prevailing at the place of use, all of which being arranged for combined purification and radiation of room air at the place of use in question.

In FIGS. 4A and 4D there is illustrated one layer of UV tubes 54n, here for example 10, and such a single layer can appropriately be located so close to the covers 57a, 57b and thereby the opening of the covers as possible, for thereby rendering a best possible and most intense UV radiation of the room surfaces to be treated. The UV radiation is further improved by the use of full gloss reflectors, for example full gloss Al foils or plates.

Further, the number of UV sources may be increased, for example to 3×10 lamps or more, and the air velocity through the arrangement 51 can then be increased from for example 1 m/s to 3 m/s, with just as favourable radiation effect for circulating air through closed arrangement. Alternatively, a UV probe can regulate the air velocity in dependence of the UV strength.

In FIGS. 6A–6D there is illustrated a free-standing mobile embodiment according to the invention. The arrangement itself is here designated by reference numeral 301, and comprises here an upper portion 302a and a lower portion 302b, wherebetween are extended a plurality of UV radiation sources 304n provided in a ring, and within the ring there is provided a cylinder-shaped combination filter, comprising a pre-filter 303, for example an EU3 filter, one or more fans 305 as well as a diffuser 306, all of which being assembled for purification and radiation of room air in the room, chamber, on the hall wherein said arrangement 301 is present.

In the upper portion 302a there is provided a control panel which can switch on and off the arrangement 301 depending upon whether human beings or animals are within the room wherein the air is to be purified and radiated, said arrangement 301 itself comprising driving means for displacing the arrangement 301 itself to various positions in the room or the chamber, for thereby achieving complete radiation of all exposed surfaces in the room in question.

It is to be understood that said means for displacing the arrangement 301 can comprise for example wire pulling means pulling the arrangement 301 along predetermined paths. Alternatively, the arrangement 301 can upon a command be displaced along various types of guiding rails or guiding antennas which appropriately can be provided in the room or in the floor or in walls or ceiling, and be equipped with auxiliary means for raising and lowering the arrangement to the positions rendering effective radiation. The arrangement 301 can also comprise means for robot control alone, for thereby being programable to an appropriate displacement pattern involving complete radiation of the room within which the arrangement resides, the air at the same time also being purified and radiated when said arrangement is in operation.

In the illustrated embodiment there is suggested a lower portion 302b comprising caster wheels 320 attached underneath a plate 321, as well as a superjacent plate 322 on which there may be attached preconnection equipment or ignition coils 323 for said UV tubes, and possibly appropriate driving means if the arrangement 301 is to fulfil its program by displacement around the room in question.

Said cylindric diffusor 306 can be constituted by a conventional metal pipe, comprising perforations, which involves that the air passing by said pre-filter 303, wherein particles larger that 1.0 $\mu$m are trapped, can be scattered along the diffusor/filter 306 and pass the UV tubes 404n arranged at a distance of approximately 25 mm, or possibly less, for thereby imposing an appropriate radiation effect on the microbes and viruses being in the air.

By means of the arrangement 301 it is possible in a fast and effective manner to effect radiation of both surfaces and the air in the room wherein the arrangement is residing, for thereby obstructing both airborne and wall settled viruses, also in the size range 0.001 $\mu$m.

It is to be understood that the upper portion 302a can comprise an IR detector 309 which cuts off possible current supply to the UV lamps 304n when a human being or an animal enters the room in question, and additionally there may be provided a special plug connection 330 which can also be interlocked via IR detector, for thereby achieving double security against damages on human beings or animals due to UV rays.

Further, it is to be understood that said control means in the upper portion 302a can be designed so as to comprise a UV probe sensing the output power from said UV tubes 304n, said means regulating the rotational speed of the fan 305 for thereby optimizing the air flow throughput through said arrangement 301, and thereby ensure optimum radiation on the detrimental particles to be found in the air.

By this mobile or partly mobile arrangement 301 it can thereby be achieved a fast and effective direct radiation with long exposure time of the surfaces to be disinfected, said disinfection of air particles being realised in a safe manner by appropriate air flow throughput and distance between the diffusor 306 and the UV tubes 304n in question.

In FIG. 7 there is illustrated a variant of the arrangement 101 wherein the housing means 102 itself comprises an inlet pipe 108 for incoming contaminated air, which air passes through a pre-filter and a crude filter 103, for example of the type 103 or 105, whereafter the air passes a plurality of UV sources 104n, whereafter the UVc radiated air passes a crude filter, for example of the type EU7, here designated by reference numeral 103a, which filter catches particles down to a size of 0.5 $\mu$m.

Downstreams of the crude filter 103a there is provided a fan chamber including a fan 105 conveying the air further on through a chamber wherein are mounted heating elements 120 for possible heating of cold outdoors air, in which chamber there also may be mounted thermostats or heating probes, which more or less preheated air thereafter passes through an absolute filter 121 catching particles down to 0.001 $\mu$m, i.e. close to the size of gas molecules, which mechanical filter may comprise fine-meshed cloth of substantial length.

Downstreams of an interspace 122 there is in the housing means 102 provided an electrostatic filter 106a, provided in a container for simple dismantling and possible cleaning by washing, whereafter there follows a bioclimatic filter 106 comprising corona discharge sources having the previously discussed function.

The purified air 113 can then via an appropriate outlet and with an appropriate over pressure be conveyed to the place intended for its application.

In FIG. 8 illustrating a first embodiment for this type of arrangement 101a, the inlet pipe 108a can be adapted so as to suck impure air to the housing means 102a in question via a plurality of branches 130n which are included in a ventilation system, for example in a restaurant or similar. In connection with a restaurant installation such branches can be designed as ornament objects 131n and/or utility objects matching the interior, it being in the restaurant, communal hall, meeting premises, etc., in question.

In FIG. 9 there is illustrated another variant of use of a corresponding arrangement 101b wherein an outlet pipe 113b starts from the housing means 102b in question including purified pressure air which via a plurality of branches 130n is blown out from said housing means 102b, said branches 130n being terminated as ornament objects 131n and/or utility objects in an appropriate living room, meeting premises, etc., and by an appropriate utilization it is possible to combine the aggregates according to FIGS. 8 and 9 such that the outdoor air 113a from the first arrangement 101a can be connected to the inlet 113b to the second arrangement 102b, possibly in combination with a heat exchanger and a fresh air inlet.

Figure 7A:
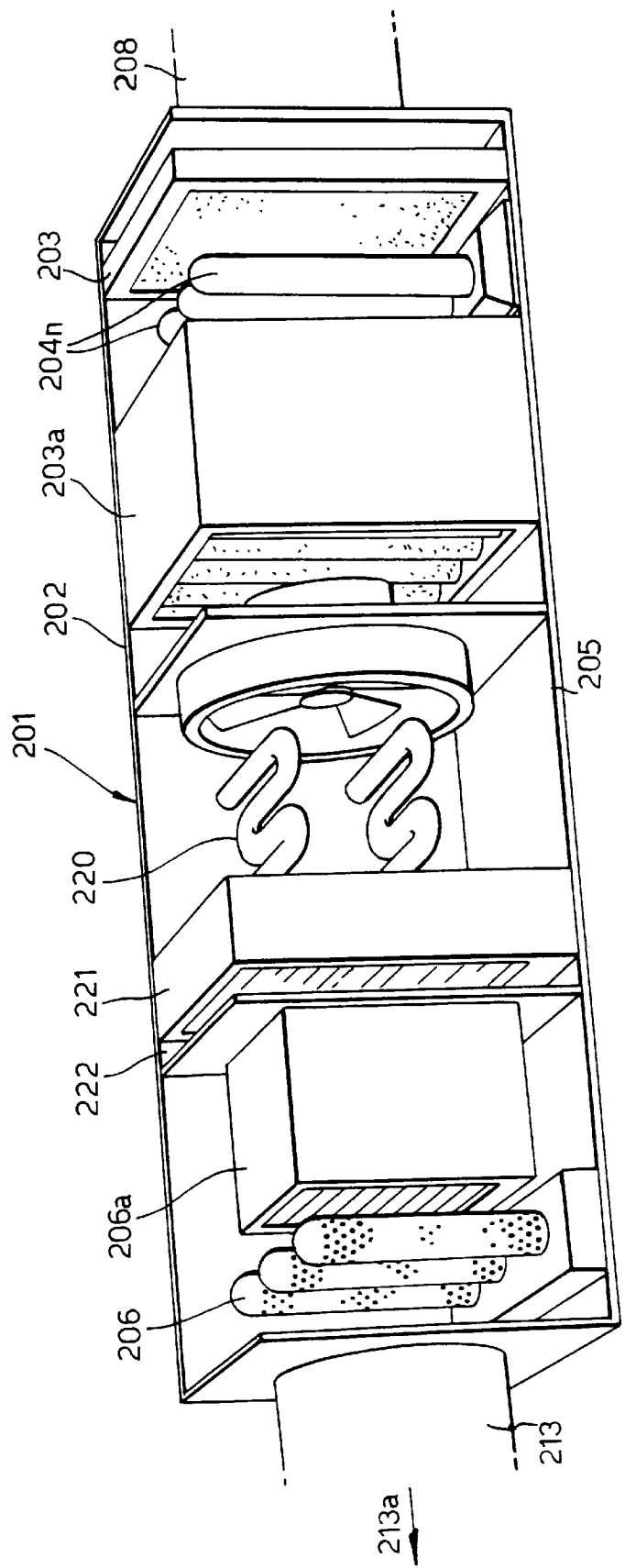
FIG. 7A illustrates further details in a variant of the embodiment according to FIG. 7.

In FIG. 7a there is further illustrated details of a variant of the embodiment according to FIG. 7, said variant being provided as an arrangement 201 wherein the housing means 202 itself which is illustrated by a section, comprises an inlet pipe 208 for incoming contaminated air which can pass through a pre-filter or crude filter 203, a plurality of UV sources 204n, a crude filter 203a, whereafter the air is guided through a fan chamber including a fan 205. In the fan chamber there is also provided heating elements 220 whereafter in the direction of flow there is mounted an absolute filter 221.

Downstreams thereof there is provided an intermediate space 222, and thereafter an electrostatic filter 206a and finally a bioclimatic filter 206 comprising corona discharge sources operating as previously discussed in connection with FIG. 7.

Figure 8A:
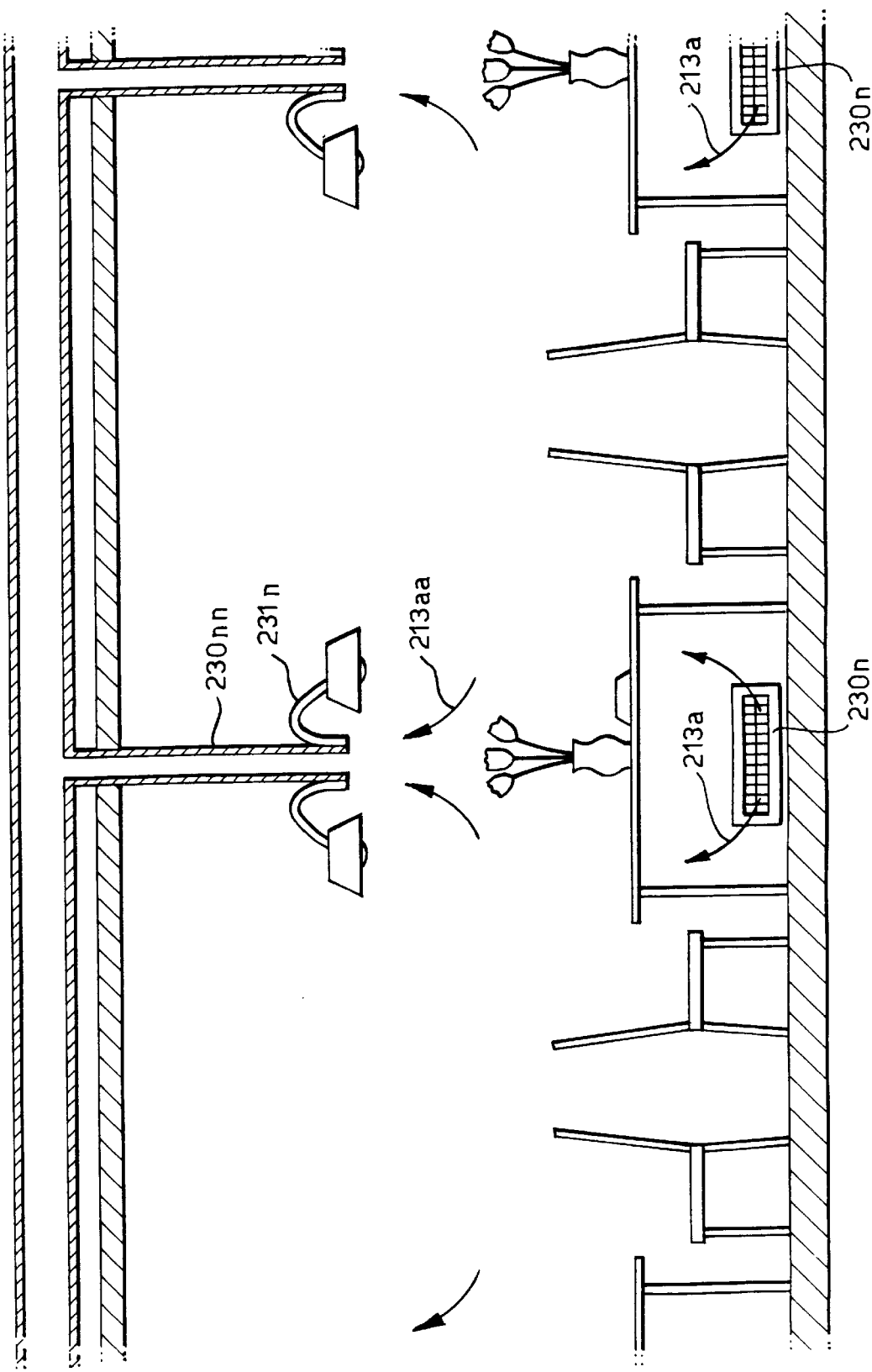
FIG. 8A illustrates an alternative installation similar to FIG. 8.

The purified air can pass via an outlet 213 and with an appropriate over pressure be guided to the place of application, for example as illustrated in FIG. 8a.

In FIG. 8a purified air 213a, for example air which has been purified through the arrangement 201 in FIG. 7a, can be supplied via appropriately located valves 230n, for example located at floor level in a restaurant or similar. Impure or used air 213aa can be sucked out via a plurality of branches 230nn included in the overall ventilation system, and which can be designed as ornament objects 231n and/or utility objects matching the interior of the premises concerned.

The outlet air 213aa can possibly be connected to the arrangement 201 illustrated in FIG. 7a, possibly in combination with heat exchanger and fresh air inlet.

I claim:

1. A device used in an air purifying system, the device comprising:
    a housing through which air flows, the housing having an inlet and an outlet;
    an ultraviolet light source positioned in said housing;
    a particulate pre-filter positioned in said housing and located upstream of said ultraviolet light source with respect to a direction of air flow;
    a post-filter positioned in said housing and located downstream of said ultraviolet light source with respect to the direction of air flow, said particulate pre-filter being located adjacent to said ultraviolet light source such that said particulate pre-filter is irradiated by said ultraviolet light source when said ultraviolet light source is activated, said particulate pre-filter also preventing ultraviolet light from said ultraviolet light source from passing through said particulate pre-filter to said inlet;
    a fan located downstream of said ultraviolet light source with respect to the direction of airflow and located upstream of said post-filter with respect to the direction of airflow:
    a cover moveable between an open position in which ultraviolet light from said ultraviolet light source is permitted to irradiate an area external of said housing and a closed position in which said ultraviolet light from said ultraviolet light source is prevented from irradiating said area external of said housing; and
    remotely controlled means which upon appropriate signal moves said cover between said closed position defining a passive mode in which air within the housing is irradiated by ultraviolet light from said ultraviolet light source and air is filtered through said particulate pre-filter and said post-filter, and said open position defining an active mode in which said area external of said housing is irradiated by ultraviolet light from said ultraviolet light source and air is filtered through at least one of said particulate pre-filter and said post-filter.

2. The device as claimed in claim 1, further comprising a detection device for detecting the presence of a human or an animal and signaling said remotely controlled means.

3. The device as claimed in claim 2, wherein said detection device includes an IR detector.

4. The device as claimed in claim 2, wherein said detection device is attached to said housing.

5. The device as claimed in claim 2, wherein said detection device is located at a location remote from said housing.

6. The device as claimed in claim 1, wherein said particulate pre-filter is an EU4 filter.

7. The device as claimed in claim 1, wherein said ultraviolet light source includes an ultraviolet tube located along a longitudinal axis of said housing.

8. The device as claimed in claim 1, wherein said post-filter includes a bioclimatic filter positioned in said housing and located downstream of said ultraviolet light source with respect to the direction of air flow.

9. The device as claimed in claim 1, wherein said post-filter includes a carbon filter located downstream of said ultraviolet light source with respect to the direction of air flow.

10. The device as claimed in claim 1, further comprising a sensor device for sensing movement and deactivating said ultraviolet light source upon sensing movement.

11. The device as claimed in claim 1, further comprising controlling means for controlling a radiation strength of said ultraviolet light source.

12. The device as claimed in claim 1, further comprising regulating means for regulating an amount of air flow through said housing.

13. The device as claimed in claim 1, in combination with a ventilation system, said system having a plurality of air duct branches for providing air to said inlet or for discharging air from said outlet.

* * * * *